US011744987B2

(12) United States Patent
Siess et al.

(10) Patent No.: US 11,744,987 B2
(45) Date of Patent: Sep. 5, 2023

(54) BLOOD PUMP WITH REINFORCED CATHETER

(71) Applicant: ABIOMED EUROPE GMBH, Aachen (DE)

(72) Inventors: Thorsten Siess, Aachen (DE); Frank Kirchhoff, Aachen (DE); Walid Aboulhosn, Aachen (DE)

(73) Assignee: Abiomed Europe GMBH, Aachen (DE)

( * ) Notice: Subject to any disclaimer, the term of this patent is extended or adjusted under 35 U.S.C. 154(b) by 636 days.

(21) Appl. No.: 16/610,743

(22) PCT Filed: May 3, 2018

(86) PCT No.: PCT/EP2018/061349
§ 371 (c)(1),
(2) Date: Nov. 4, 2019

(87) PCT Pub. No.: WO2018/202775
PCT Pub. Date: Nov. 8, 2018

(65) Prior Publication Data
US 2020/0094019 A1   Mar. 26, 2020

(30) Foreign Application Priority Data

May 4, 2017   (EP) .................................... 17169486

(51) Int. Cl.
*A61M 25/01*   (2006.01)
*A61M 60/857*   (2021.01)
(Continued)

(52) U.S. Cl.
CPC ........ *A61M 25/0102* (2013.01); *A61M 60/13* (2021.01); *A61M 60/216* (2021.01);
(Continued)

(58) Field of Classification Search
CPC ............ A61M 25/0102; A61M 25/005; A61M 25/0155; A61M 60/135; A61M 60/148;
(Continued)

(56) References Cited

U.S. PATENT DOCUMENTS 4,909,787 A * 3/1990 Danforth ............. A61M 25/104
604/95.03
5,336,178 A * 8/1994 Kaplan ................. A61M 29/02
604/913

(Continued)

FOREIGN PATENT DOCUMENTS

CN   103536384 A   1/2014
JP   2009506839 A   2/2009
(Continued)

OTHER PUBLICATIONS

"Reproducibility of Aorta Segmentation on 4D Flow MRI in Healthy Volunteers", Juffermans, J.F., et al., J. Magn. Reson. Imaging 2021;53:1268-1279 (Year: 2020).*

(Continued)

*Primary Examiner* — Nathan R Price
*Assistant Examiner* — Adam J. Cermak
(74) *Attorney, Agent, or Firm* — Botos Churchill IP Law LLP

(57) ABSTRACT

An intravascular blood pump may have a catheter (10) and a pumping device (1) attached to the catheter (10). The catheter (10) extends along a longitudinal axis and has a distal end (11) and a proximal end (12) opposite the distal end (11). The catheter (10) may have a tubular stiffening structure (15) extending longitudinally between the proximal end (12) and the distal end (11) of the catheter (10). The tubular stiffening structure (15) has a lumen (21) and a proximal end (17) and a closed distal end (16) opposite the proximal end (17), wherein the lumen (21) of the stiffening (Continued)

structure (15) is configured to receive a pressurized fluid having an over-pressure of at least 5 bar.

6 Claims, 3 Drawing Sheets

(51) Int. Cl.
  *A61M 60/216* (2021.01)
  *A61M 60/829* (2021.01)
  *A61M 60/13* (2021.01)
  *A61M 25/00* (2006.01)

(52) U.S. Cl.
  CPC ........ *A61M 60/829* (2021.01); *A61M 60/857* (2021.01); *A61M 25/005* (2013.01); *A61M 2205/0266* (2013.01); *A61M 2210/125* (2013.01)

(58) Field of Classification Search
  CPC ........ A61M 60/857; A61M 2205/0266; A61M 2210/125; A61M 2025/0915; A61L 29/02; A61L 29/04
  See application file for complete search history.

(56) References Cited

U.S. PATENT DOCUMENTS

| | | | | |
|---|---|---|---|---|
| 6,508,777 | B1* | 1/2003 | Macoviak | A61M 1/3659 604/9 |
| 6,544,216 | B1* | 4/2003 | Sammler | A61M 25/0125 604/95.03 |
| 7,736,323 | B2* | 6/2010 | Von Weymarn-Scharli | A61M 25/0127 604/524 |
| 9,439,721 | B2* | 9/2016 | Werneth | A61B 18/1492 |
| 9,474,840 | B2* | 10/2016 | Siess | G01L 9/0079 |
| 9,669,142 | B2* | 6/2017 | Spanier | A61B 5/02154 |
| 9,669,144 | B2* | 6/2017 | Spanier | A61M 25/01 |
| 9,833,550 | B2* | 12/2017 | Siess | A61M 60/135 |
| 9,889,273 | B2* | 2/2018 | Cully | A61M 25/0102 |
| 10,808,704 | B2* | 10/2020 | Siess | F04D 13/0626 |
| 10,835,112 | B2* | 11/2020 | Smith | A61B 1/0057 |
| RE48,649 | E* | 7/2021 | Siess | A61B 5/02154 |
| 11,266,811 | B2* | 3/2022 | Friend | A61B 1/015 |
| 11,413,446 | B2* | 8/2022 | Siess | A61M 60/857 |
| 2005/0228274 | A1* | 10/2005 | Boese | A61M 25/0105 604/95.04 |
| 2006/0264907 | A1* | 11/2006 | Eskridge | A61M 25/0023 604/528 |
| 2007/0016133 | A1* | 1/2007 | Pepper | A61M 25/10 604/103.04 |
| 2007/0060880 | A1* | 3/2007 | Gregorich | A61M 25/0097 604/95.04 |
| 2007/0100235 | A1* | 5/2007 | Kennedy, II | A61M 25/0136 600/152 |
| 2007/0282302 | A1* | 12/2007 | Wachsman | A61F 2/958 604/509 |
| 2011/0040282 | A1* | 2/2011 | Uihlein | A61M 25/0043 604/525 |
| 2011/0166515 | A1 | 7/2011 | Nour | |
| 2012/0226103 | A1* | 9/2012 | Gunday | A61B 1/015 604/95.01 |
| 2013/0116701 | A1* | 5/2013 | Wang | A61M 25/0069 606/108 |
| 2014/0194857 | A1* | 7/2014 | Eilat | A61M 25/0017 604/544 |
| 2014/0276642 | A1* | 9/2014 | Cully | A61M 25/0053 604/525 |
| 2015/0018802 | A1* | 1/2015 | Zvuloni | A61M 25/008 604/517 |
| 2015/0080743 | A1* | 3/2015 | Siess | A61M 60/135 600/478 |
| 2015/0087890 | A1* | 3/2015 | Spanier | A61M 60/139 600/16 |
| 2015/0273181 | A1* | 10/2015 | Leeflang | A61M 25/005 606/41 |
| 2015/0328382 | A1* | 11/2015 | Corbett | A61M 60/865 600/16 |
| 2016/0213827 | A1* | 7/2016 | Tanner | A61M 60/13 |
| 2016/0271363 | A1* | 9/2016 | Bauer | A61M 25/0043 |
| 2016/0317790 | A1 | 11/2016 | Ruebben | |
| 2017/0157361 | A1* | 6/2017 | Barrish | A61M 25/0155 |
| 2018/0001003 | A1* | 1/2018 | Moran | A61M 25/0662 |
| 2018/0015257 | A1* | 1/2018 | Krolik | A61F 2/915 |

FOREIGN PATENT DOCUMENTS

| | | | | |
|---|---|---|---|---|
| JP | 2010536522 A | 12/2010 | | |
| WO | WO-9403229 A1 * | 2/1994 | ........ | A61M 25/0068 |
| WO | WO-9958174 A2 * | 11/1999 | ........ | A61M 1/3653 |
| WO | 0053239 A1 | 9/2000 | | |
| WO | 0183016 A2 | 11/2001 | | |
| WO | 2011035925 A1 | 3/2011 | | |
| WO | WO-2011039091 A * | 4/2011 | ........ | A61B 5/02154 |

OTHER PUBLICATIONS

International Search Report and Written Opinion for corresponding International Application No. PCT/EP2018/061349 dated Jul. 9, 2018 (21 pages).
Office Action from corresponding Chinese Patent Application No. 201880029851.5 dated Oct. 27, 2021 (21 pages).
Extended European Search Report for corresponding European Patent Application No. 21 209 718.2 dated Apr. 14, 2022 (7 pages).
Office Action from corresponding Chinese Application No. 201880029851.5 dated Sep. 2, 2022 (13 pp.).
Office Action from corresponding Chinese Patent Application No. 201880029851.5 dated May 5, 2022 (22 pp.).
Office Action in corresponding Japanese Patent Application No. 2019-560767 dated May 10, 2022 (14 pp.).
Office Action from corresponding Israeli Patent Application No. 270055 dated Jun. 11, 2023 (8 pp.).

* cited by examiner

BLOOD PUMP WITH REINFORCED CATHETER

CROSS-REFERENCE TO RELATED APPLICATIONS

This application is a United States National Stage filing under 35 U.S.C. § 371 of International Application No. PCT/EP2018/061349, filed May 3, 2018, which claims priority to European Patent Application No. 17169486.2, filed May 4, 2017. The contents of each of each of the foregoing applications are hereby incorporated by reference in their entirety. International Application No. PCT/EP2018/061349 was published under PCT Article 21(2) in English.

BACKGROUND

This invention relates to an intravascular blood pump for percutaneous insertion into a patient's blood vessel, comprising a catheter and a pumping device attached to the distal end of the catheter.

Blood pumps for percutaneous insertion are designed to support a patient's heart and are inserted into a patient's heart via a blood vessel such as the aorta or femoral artery by means of a catheter through a vascular access in the patient's skin, i.e., percutaneously. An intravascular blood pump for percutaneous insertion typically comprises a catheter and a pumping device attached to the catheter. The catheter may extend along a longitudinal axis from a distal end to a proximal end, with the pumping device being attached to the catheter at the end remote from an operator, such as a surgeon. The pumping device may be inserted e.g., through the femoral artery and the aorta into the left ventricle of a patient's heart by means of the catheter. Blood pumps which are placed in a patient's heart may also be referred to as intracardiac blood pumps.

A relatively stiff catheter bears less risk of kinking, whereas a soft catheter better adapts to the shape of a blood vessel such as the aorta, in particular the aortic arch. However, soft catheters tend to kink in particular during insertion of the catheter because of their low rigidity. Once a catheter has kinked, this creates a weakened location on the catheter and it will most likely kink at the same location again. This may become particularly problematic during operation of the blood pump. For example, the blood pump may be pushed out of the heart back into the aorta, which may cause the catheter to kink, in particular if the catheter already kinked during insertion. This may result in a sharp kink at the weakened location, which in turn causes kinking of structures inside the catheter, such as a purge line that supplies purge fluid to the pumping device. The purge line can block and the blood pump can fail due to increased purge pressure or even complete blocking of the purge line.

Attempts have been made to reinforce or stiffen the catheter, but the resulting stiffness may be undesirable. Other attempts have been made to reinforce e.g., only the purge line, which may increase the complexity of the construction and cause higher costs. Apart from that, it would be desirable to be able to adjust the stiffness of the catheter.

SUMMARY OF THE INVENTION

It is therefore an object of the present invention to provide an intravascular blood pump for percutaneous insertion into a patient's vessel having a catheter which can be prevented from kinking, whereby the stiffness of the catheter can be adjusted.

This object is achieved according to the present invention by a blood pump for percutaneous insertion having the features of independent claim 1. Preferred embodiments and further developments of the invention are specified in the claims dependent thereon. Throughout this disclosure, the term "distal" will refer to directions away from a user and towards the heart, whereas the term "proximal" will refer to directions towards a user.

According to the invention, the catheter of an intravascular blood pump for percutaneous insertion comprises a tubular stiffening structure that extends longitudinally between the proximal end and the distal end of the catheter. The tubular stiffening structure has a lumen and a proximal end and a closed distal end opposite the proximal end. The lumen of the stiffening structure is configured to receive a pressurized fluid having an over-pressure of at least 5 bar. The closed distal end permits the lumen to receive and hold a pressurized fluid such that the stiffness of the stiffening structure can be adjusted. The stiffening structure may have a predetermined stiffness with no pressurized fluid received in the lumen, it being possible to increase the stiffness by inserting a fluid and increasing the pressure in the fluid.

The tubular stiffening structure allows for adjustment of its bending stiffness by increasing or decreasing the pressure of the pressurized fluid inside the lumen of the tubular stiffening structure. Pressurized fluid can be inserted from the proximal end and is prevented from exiting the tubular stiffening structure because the distal end is closed. For example, pressurized fluid can be inserted into and kept inside the lumen of the tubular stiffening structure with a high pressure during insertion of the catheter into a patient's blood vessel, where the catheter should have a high bending stiffness. Pressure can be released once the catheter is inserted to a desired amount, resulting in a decreased bending stiffness, which allows the catheter to better conform to the shape of the blood vessel. A user can adjust the bending stiffness by adjusting the pressure of the pressurized fluid at any time depending on the application and the needs.

The stiffening structure can prevent the catheter from kinking while at the same time providing sufficient flexibility to enable bending so that the catheter can be directed through a blood vessel, such as the aorta. Kinks can be prevented particularly during insertion of the blood pump whereby a surgeon/cardiologist pushes the catheter through the blood vessel. Weakened locations on the catheter are avoided such that there is less risk of the catheter kinking during operation of the blood pump. Should a catheter kink during the procedure nevertheless, then it will have a chance to flex back and the catheter can recover its shape over time. In particular, since a kink is a plastic deformation of the catheter, i.e., a nonreversible deformation, whereas bending is an elastic deformation where the catheter can return to its initial shape, the stiffening structure preferably allows the catheter to be elastically deformed with a bending radius of 10 mm or less without the occurrence of plastic deformation. The bending radius is measured with respect to a central axis of the catheter.

For example, the stiffness of the catheter can be increased during insertion of the catheter for facilitating insertion and for avoiding kinks in the catheter during insertion, and decreased during operation of the blood pump to allow the catheter to adjust to the shape of the blood vessel. Preferably, the lumen of the stiffening structure is configured to receive a pressurized fluid having an over-pressure of between 5 bar and 150 bar, for instance 75 bar. More specifically, the lumen of the stiffening structure may be configured to receive a pressurized fluid having an over-pressure of at least 5 bar, at least 10 bar, at least 20 bar, at least 30 bar or even higher pressures of at least 50 bar, at least 85 bar, or at least 100 bar, up to 150 bar to achieve a desired stiffness.

The stiffening structure may be configured to stay in the catheter during operation of the blood pump in order to support the catheter and prevent kinks during the entire surgical procedure and during operation of the blood pump. This may be advantageous in applications in which the blood pump tends to be pushed out of the heart during operation of the blood pump, either by movements of the heart or by the pumping action of the blood pump. In applications in which there is no or less tendency of pushing the blood pump out of the heart the stiffening structure may be configured to be removed from the catheter after placement of the blood pump in the patient's body. This renders the catheter more flexible during operation of the blood pump and allows the catheter to better adapt to the shape of the respective vessel, such as the aorta. This reduces contact between the inner wall of the vessel and the catheter and may also reduce the force with which the pump may push against a valve structure.

A typical length of a catheter for percutaneous insertion via a femoral access (arterial or venous) into the patient's heart can be between 100 to 150 cm. The stiffening structure can also have a length between 100 and 150 cm. The catheter and stiffening structure may have a length between 25 and 50 cm in case the catheter is designed for insertion through the subclavian or axillary artery into the left ventricle or through the jugular vein into the right ventricle (RV, FIG. 1).

The catheter may have a lumen that extends from the proximal end to the distal end through the catheter. The stiffening structure is preferably disposed inside the lumen of the catheter. Thus, a common catheter can be used and provided with the stiffening structure by insertion of the stiffening structure through the catheter lumen. Preferably, the stiffening structure is substantially free-floating or loose, i.e., not fixed inside the lumen of the catheter. Particularly the distal end of the stiffening structure may be free, i.e., not attached to or operatively connected to other parts of the blood pump, e.g., the pumping device. This enhances flexibility of the catheter while at the same time effectively preventing the catheter from kinking because the stiffening structure may move and slide inside the catheter lumen when the catheter is bent to follow a shape of a blood vessel. This has the further effect that the flexibility of the catheter may have an isotropic behavior, i.e., the flexibility may be identical in any bending direction, because the stiffening structure is not fixedly attached to one side of the catheter.

Alternatively, the stiffening structure may be contained or embedded in a wall of the catheter or placed on an outer surface of the catheter rather than being inserted into the lumen of the catheter. The stiffening structure may be fixed at least in a radial direction. It may be movable in an axial direction to be able to slide in the axial direction along the length of the catheter e.g., when the catheter is bent. For instance, the stiffening structure may be secured on the outer surface of the catheter by means of any suitable attachments, like rings, loops, eyelets or the like. Alternatively, the stiffening structure may be fixed on the outer surface of the catheter along its entire length.

The stiffening structure preferably comprises or is made of a shape-memory material, preferably a shape-memory alloy, for example Nitinol, having superelastic properties. The material may alternatively comprise a polymer material, which can also have shape-memory properties. Shape memory materials have temperature dependent properties and temperature independent properties. Shape memory is a temperature dependent property that allows the shape memory material the ability to undergo deformation at one temperature and then recover its original, undeformed shape upon heating above its "transformation temperature". The temperature change causes a transformation between the martensite phase and austenite phase of the material. Superelasticity is a temperature independent property that allows the shape memory material the ability to undergo a mechanical deformation due to an external force applied to the shape memory material, and then recover its original undeformed shape upon release of the external force. The superelasticity, which is also referred to as pseudoelasticity, is caused by a transformation between the martensite phase and the austenite phase that occurs due to external loads. As a result, these materials can reversibly deform to very high strains. It will be appreciated that other materials are possible as long as they are suitable to hold the pressurized fluid within the lumen of the tubular stiffening structure.

The stiffening structure may also be braided. More specifically, if the stiffening structure comprises at least three tube, the tubes may be braided, either forming a substantially solid braid or a braided tube, i.e., a hollow tubular body. The stiffening structure may comprise at least two tubes that are twisted.

In one embodiment, a system comprises a blood pump as described above and a pressure source that is connected to the proximal end of the stiffening structure and configured to supply pressurized fluid to the lumen of the stiffening structure. The system may further comprise a controller that is configured to adjust the pressure of the pressurized fluid, in particular in the aforementioned range. The fluid is preferably a highly viscous, biocompatible fluid, such as glycerin, silicon oils or gels or saline. High viscous fluids are preferred because they are less likely to leak out of the tubular stiffening structure than low viscous fluids.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
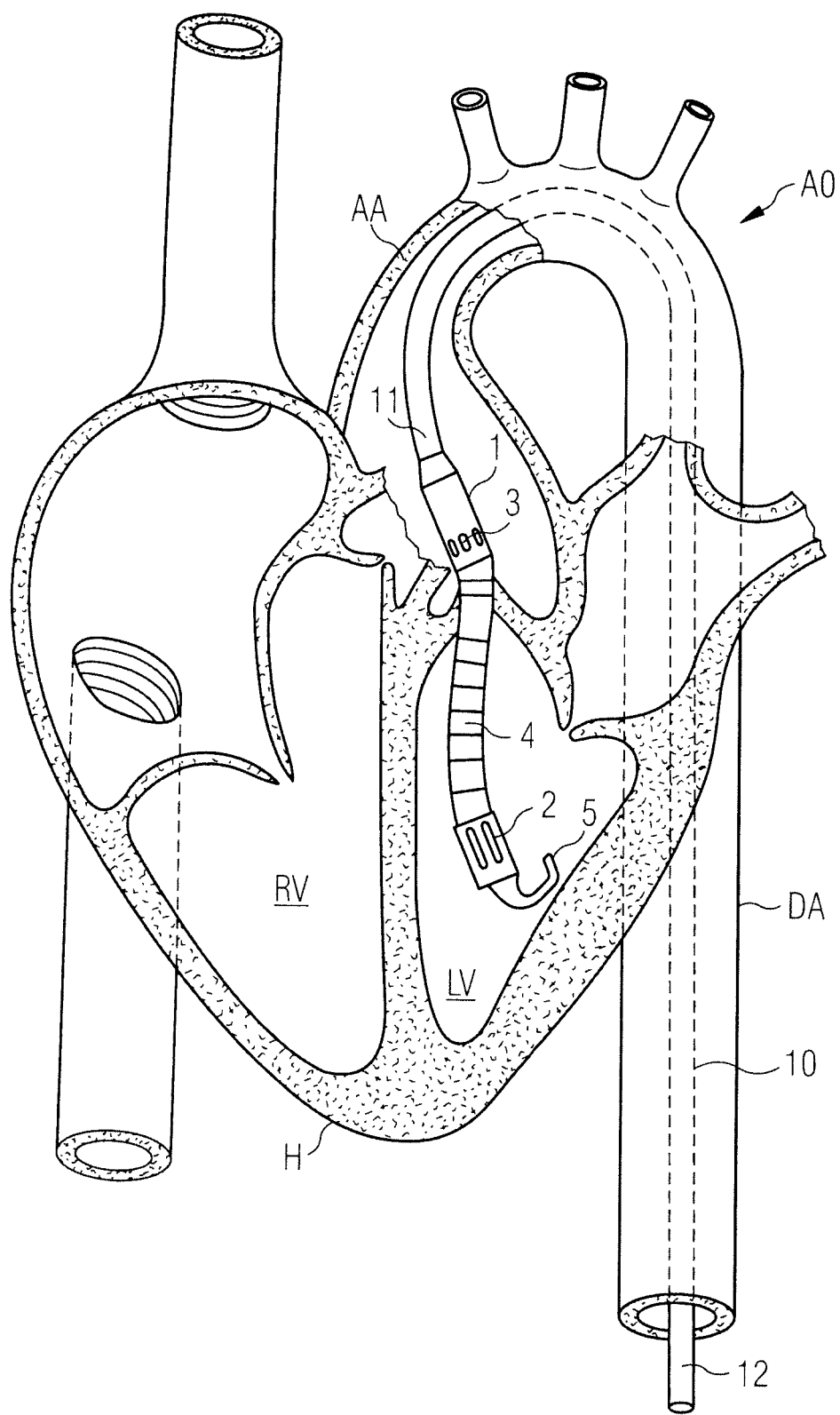
FIG. 1 shows a patient's heart with a blood pump inserted through the aorta into the left ventricle.

In FIG. 1 is illustrated a blood pump inserted into a patient's heart H. More specifically, the blood pump comprises a pumping device 1 attached to a catheter 10 by means of which the pumping device 1 is inserted into the left ventricle LV of the patient's heart H via the aorta AO, including the descending aorta DA and the aortic arch AA. The catheter 10 has a distal end 11 and a proximal end 12. The blood pump has a blood flow outlet 3 that is disposed outside the patient's heart H in the aorta AO, while a blood flow inlet 2 is in flow communication with a flow cannula 4 placed inside the left ventricle LV. An impeller (not shown) is provided in the pumping device 1 to cause the blood flow from the blood flow inlet 2 to the blood flow outlet 3. At the distal end of the blood pump, a soft tip 5, such as a pigtail or J-tip, is arranged to facilitate insertion of the blood pump into the patient's heart H without causing any harm to the surrounding tissue. Also, the soft tip 5 helps to keep soft tissue away from the blood flow inlet 2 and to support the pumping device 1 against the inner wall of the left ventricle LV.

Figure 2:
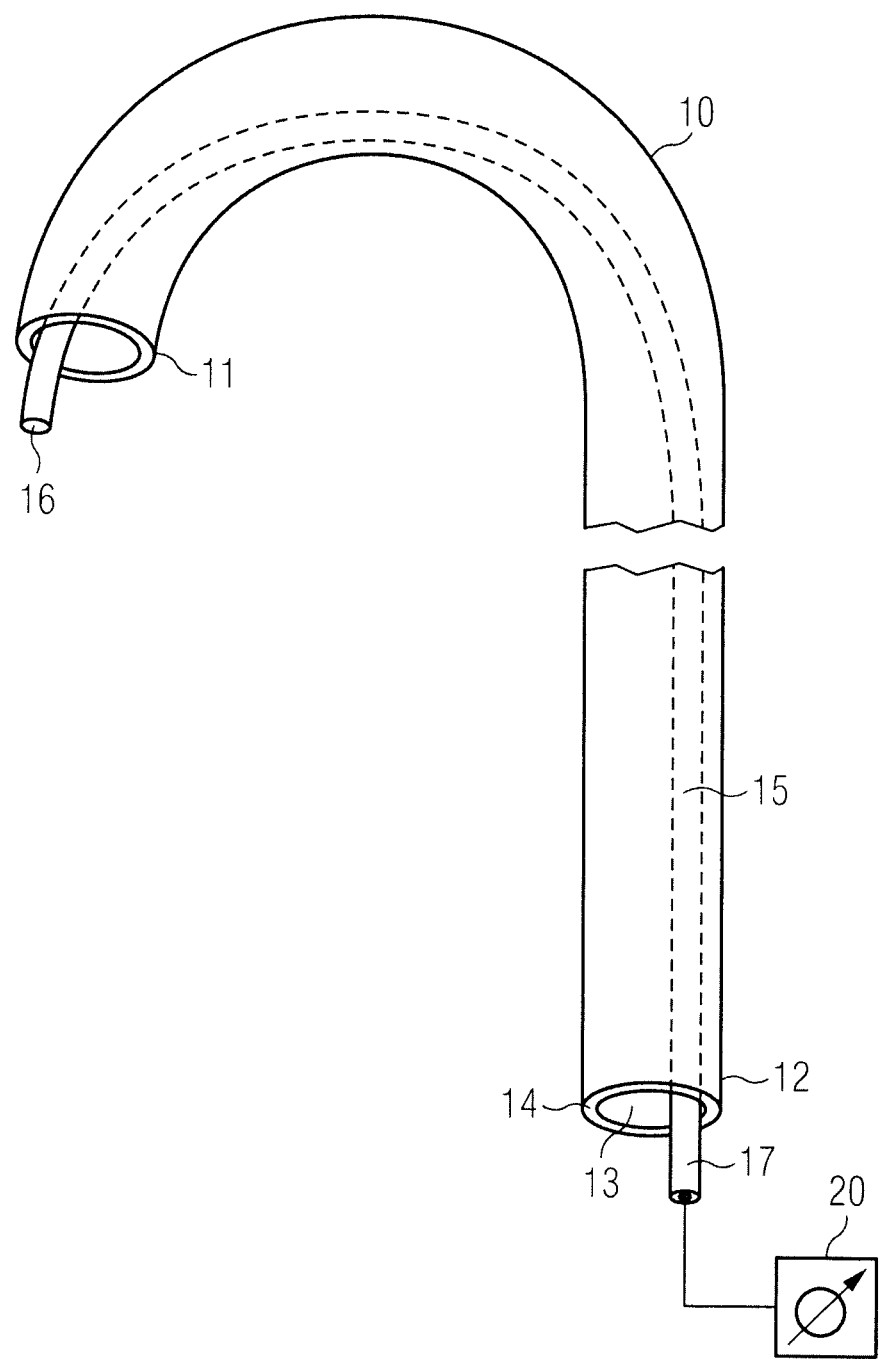
FIG. 2 schematically shows the catheter of the blood pump of FIG. 1 with a stiffening structure.

Referring now to FIG. 2, the catheter 10 of the blood pump of FIG. 1 is shown. The catheter 10 extends from the distal end 11 to the proximal end 12 and has a lumen 13 that extends through the catheter 10. The pumping device 1 which is attached to the distal end 11 of the catheter 10 as shown in FIG. 1 is not shown in FIG. 2. The lumen 13 of the catheter 10 is defined by a wall 14 of the catheter 10, which may have a wall thickness of about 0.1 to 1 mm, such as 0.5 mm. The catheter 10 may have an outer diameter of 2 mm to 4 mm, such as about 3 mm (corresponding to a dimension of 9 French). Accordingly, the inner diameter of the catheter may be for instance about 2 mm (corresponding to a dimension of 7 French). A tubular stiffening structure 15 is disposed inside the catheter lumen 13 and extends from a distal end 16 to a proximal end 17. It extends continuously through the catheter 10 from the catheter's distal end 11 to its proximal end 12. Other structures that may extend through the catheter 10, such as a purge line or electric wire, are omitted in FIG. 2 for the sake of clarity.

Figure 3:
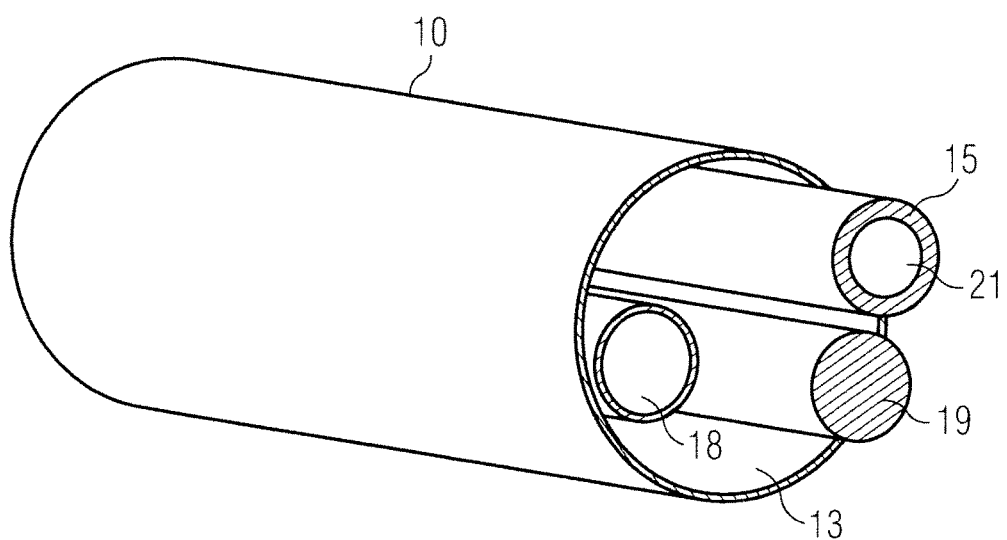
FIG. 3 schematically shows the catheter with a stiffening structure in accordance with one embodiment.

FIG. 3 shows a schematic view of the catheter 10. The tubular stiffening structure 15 is disposed inside the catheter lumen 13 along with a purge fluid line 18 for supplying a purge fluid to the pumping device 1 and an electric wire 19 for supplying electric power to the pumping device 1. The stiffening structure 15 is particularly useful for preventing the purge line 18 from kinking, which would occlude the purge line 18 and lead to failure of the blood pump because the purge pressure is too high or lubricating is interrupted. It will be appreciated that more than one tube, such as two or three, may be provided. The one or more tubes may be identically formed with respect to size and shape or may have different sizes and shapes. The tubular stiffening structure 15 preferably comprises a shape-memory material, such as Nitinol. However, other materials may also be used, such polymeric materials with or without shape-memory characteristics. The tube 15 may also be braided. More specifically, the stiffening structure 15 may comprise at least two, preferably three or more, tubes 15 that are twisted or preferably braided, to form e.g., a substantially solid twist or braid or a braided hollow tubular member.

The tube 15 provides a kink resistance that is variable, as described in more detail below, in order to prevent the catheter 10 from kinking while permitting the catheter 10 to bend to adapt to the shape of the blood vessel, such as the aorta AO, in particular the aortic arch AA. As illustrated in FIGS. 2 and 3, the tube 15 is substantially free-floating in the lumen 13 of the catheter 10, i.e., loose and not fixed inside the catheter 10. Thus, it may follow a slightly different radius of curvature than the catheter 10 while moving inside the catheter lumen 13. The tube 15 is also permitted to slide inside the lumen 13, in particular axially, which may be advantageous for the flexibility of the catheter 10. The distal end 16 of the tube 15 is free, in particular not attached to the pumping device 1 or parts of the pumping device 1. At least the distal end 16 of the tube 15 may be protected or encapsulated with a soft tip to avoid penetration into the catheter 10 or other adjacent structures.

Figure 4:
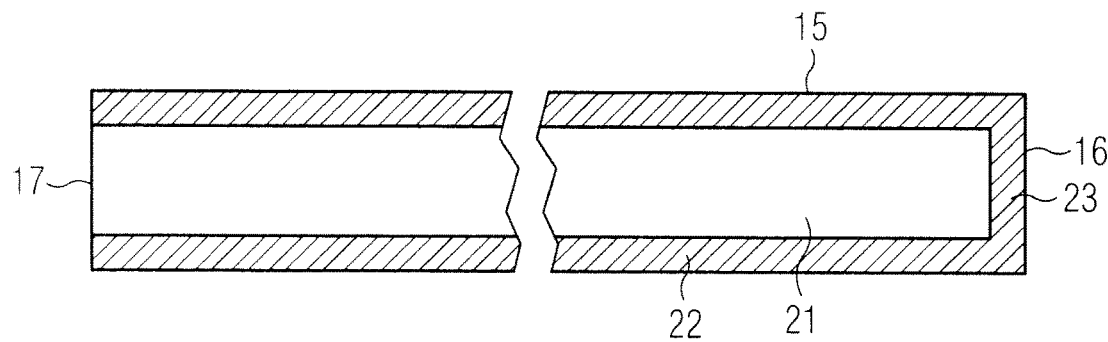
FIG. 4 shows a cross-sectional schematic view of the catheter.

As also schematically illustrated in FIG. 2, pressure source 20 with a control unit is connected to the proximal end 17 of the tube 15 in order to supply pressurized fluid to the tube 15. Also referring to FIG. 4, the proximal end 17 of the tube 15 is open and connected to the pressure source 20, whereas the distal end 16 is closed to form a lumen 21 that is able to receive and hold the pressurized fluid. The lumen 21 is, thus, limited by a circumferential outer wall 22 and an end wall 23 of the tube 15. The stiffness of the tube 15 can be adjusted by adjusting the pressure of the pressurized fluid in the lumen 21. For example, the stiffness can be increased during insertion of the blood pump into the patient's blood vessel, and decreased during operation of the blood pump, such that the catheter 10 better adapts to the shape of the patient's blood vessel, in particular the aortic arch AA. High pressures may be applied to achieve a desired stiffness, e.g., more than 5 bar or more than 30 bar, or even higher pressures of more than 50 bar or more than 75 bar, up to 150 bar. High viscous, biocompatible materials, such as glycerin, silicone oils or gels, are preferred because low viscous fluids, such as water, are more likely to leak out of the tubular stiffening structure 15.

Regardless of its shape, size and configuration, the stiffening structure 15 may comprise or may be made of a shape-memory material, preferably a shape-memory alloy, in particular Nitinol. Not least because of this material and depending on the pressure of the pressurized fluid, the stiffening structure 15 allows the catheter 10 to be bent, i.e., elastically deformed, with a bending radius of 10 mm or less without kinking, i.e., without the occurrence of plastic deformation. The bending radius is measured with respect to a central axis of the catheter. Thus, the catheter 10 with the stiffening structure 15 provides a better kink resistance. Preventing kinking of the catheter is important, for instance to avoid occlusion of tubular lines inside the catheter.

The invention claimed is:

1. An intravascular blood pump for percutaneous insertion into a patient's blood vessel, comprising:
  a catheter; and
  a pumping device attached to the catheter, the catheter extending along a longitudinal axis and having a distal end and a proximal end opposite the distal end along the longitudinal axis, the catheter comprising:
    a tubular stiffening structure having a length and extending longitudinally between the proximal end and the distal end of the catheter, the tubular stiffening structure having a lumen, a proximal end and a closed distal end opposite the proximal end,
    wherein the lumen of the tubular stiffening structure is configured to receive a pressurized fluid having an over-pressure of at least 5 bar,
    wherein the tubular stiffening structure comprises at least two of the tubular stiffening structure, and
    wherein the at least two of the tubular stiffening structure are twisted.

2. An intravascular blood pump for percutaneous insertion into a patient's blood vessel, comprising:
  a catheter; and
  a pumping device attached to the catheter, the catheter extending along a longitudinal axis and having a distal end and a proximal end opposite the distal end along the longitudinal axis, the catheter comprising:
    a tubular stiffening structure having a length and extending longitudinally between the proximal end and the distal end of the catheter, the tubular stiffening structure having a lumen, a proximal end and a closed distal end opposite the proximal end, wherein the lumen of the tubular stiffening structure is configured to receive a pressurized fluid having an over-pressure of at least 5 bar, wherein the tubular stiffening structure comprises at least three of the tubular stiffening structure, and wherein the at least three of the tubular stiffening structure are braided to form a solid braid or a braided hollow tubular member.

3. An intravascular blood pump for percutaneous insertion into a patient's blood vessel, comprising:

a catheter; and a pumping device attached to the catheter, the catheter extending along a longitudinal axis and having a distal end and a proximal end opposite the distal end along the longitudinal axis, the catheter comprising:

a tubular stiffening structure having a length and extending longitudinally between the proximal end and the distal end of the catheter, the tubular stiffening structure further having a lumen, a proximal end, and a closed distal end opposite the proximal end, wherein the lumen of the tubular stiffening structure is configured to receive a pressurized fluid having an over-pressure of at least 5 bar, and wherein the tubular stiffening structure comprises at least two tubular stiffening structures, the at least two of the tubular stiffening structure being twisted or braided.

4. The intravascular blood pump of claim 3, wherein the at least two tubular stiffening structures are twisted or braided to form a solid braid or braided hollow tubular member.

5. The intravascular blood pump of claim 3, wherein the lumen of the tubular stiffening structure is configured to receive a pressurized fluid having an over-pressure of between 5 bar and 150 bar.

6. The intravascular blood pump of claim 3, wherein the tubular stiffening structure is configured to allow the catheter to be elastically deformed with a bending radius of 10 mm or less without plastic deformation.

* * * * *